(12) United States Patent
Reimer et al.

(10) Patent No.: US 6,365,790 B2
(45) Date of Patent: Apr. 2, 2002

(54) PREPARATION OF $C_{10}$-$C_{30}$-ALKENES BY PARTIAL HYDROGENATION OF ALKYNES OVER FIXED-BED SUPPORTED PALLADIUM CATALYSTS

(75) Inventors: Klaus Reimer, Mutterstadt; Gerd Kaibel, Lampertheim; Ulrich Kammel, Speyer; Franz Josef Bröcker, Ludwigshafen; Andreas Ansmann, Wiesloch; Heinz Etzrodt, Neustadt; Manfred Stroezel, Ilvesheim; Mathias Haake, Mannheim; Lothar Laupichler, Frankenthal; Bernhard Bockstiegel, Römerberg, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/734,024

(22) Filed: Dec. 12, 2000

(30) Foreign Application Priority Data

Dec. 23, 1999 (DE) .......................... 199 62 907

(51) Int. Cl.⁷ .................... C07C 29/00; C07C 31/18; C07C 27/04; C07C 5/00; C07C 5/05
(52) U.S. Cl. .................. 568/909.5; 568/857; 568/885; 585/250; 585/273
(58) Field of Search .............. 568/909.5, 857, 568/885; 585/273, 250

(56) References Cited

U.S. PATENT DOCUMENTS

| | | | | |
|---|---|---|---|---|
| 2,681,938 A | | 6/1954 | Landlar ........... | 260/611 |
| 2,809,215 A | | 10/1957 | Surmatis et al. ....... | 260/593 |
| 4,001,344 A | | 1/1977 | Hoffmann et al. ...... | 260/635 |
| 5,750,806 A | * | 5/1998 | Brocker et al. ........ | 568/909.5 |
| 5,866,734 A | * | 2/1999 | Flick et al. ........... | 585/260 |
| 6,002,047 A | | 12/1999 | Jansen et al. .......... | 568/395 |

FOREIGN PATENT DOCUMENTS

| | | |
|---|---|---|
| DE | 24 31 929 | 1/1976 |
| DE | 26 05 641 | 11/1976 |
| DE | 26 19 660 | 11/1976 |
| EP | 412 415 | 2/1991 |
| EP | 754 664 | 1/1997 |
| EP | 827 944 | 3/1998 |
| EP | 841 314 | 5/1998 |
| GB | 871804 | 6/1961 |
| JP | 6120657 | 9/1991 |

OTHER PUBLICATIONS

Freifelder et al. "Practical Catalytic Hydrogenation" Wiley Interscience (1971) pp. 84–126.
Eitl et al. "Organic Reactions" Handbook of Heterogeneous Catalysts (1997) p. 2172.

* cited by examiner

*Primary Examiner*—Samuel Barts
*Assistant Examiner*—Eluis O. Price
(74) *Attorney, Agent, or Firm*—Keil & Weinkauf

(57) ABSTRACT

Alkenes are prepared by partial hydrogenation of alkynes in the liquid phase at from 20 to 250° C. and hydrogen partial pressures of from 0.3 to 200 bar over fixed-bed supported palladium catalysts which are obtainable by heating the support material in the air, cooling, applying a palladium compound and, if required, additionally other metal ions for doping purposes, molding and processing to give monolithic catalyst elements, by a process in which A) alkynes of 10 to 30 carbon atoms are used as starting compounds, B) the palladium compound and, if required, the other metal ions are applied to the support material by impregnation of the heated and cooled support material with a solution containing palladium salts and, if required, other metal ions and subsequent drying, and C) from 10 to 2000 ppm of carbon monoxide (CO) are added to the hydrogenation gas or a corresponding amount of CO is allowed to form in the liquid phase by slight decomposition of a compound which is added to the reaction mixture and eliminates CO under the reaction conditions.

The process is particularly advantageous if the partial hydrogenation is carried out in a tube reactor by the trickle-bed or liquid phase procedure with product recycling at cross-sectional loadings of from 20 to 500 $m^3/m^2$*h. The process is particularly suitable for the preparation of 3,7,11,15-tetramethyl-1-hexadecen-3-ol (isophytol), 3,7,11-trimethyl-1-dodecen-3-ol (tetrahydronerolidol), 3,7,11-trimethyl-1,4-dodecadien-3-ol, 3,7,11-trimethyl-1,6-dodecadien-3-ol (dihydronerolidol), 3,7-dimethyloct-1,6-dien-3-ol or 3,7-dimethyloct-1-en-3-ol from the corresponding alkynes.

12 Claims, No Drawings

PREPARATION OF $C_{10}$-$C_{30}$-ALKENES BY PARTIAL HYDROGENATION OF ALKYNES OVER FIXED-BED SUPPORTED PALLADIUM CATALYSTS

The present invention relates to a very advantageous process for the industrial production of relatively high molecular weight alkenes, in particular of monosubstituted alkenes, by partial hydrogenation of the corresponding alkynes in the liquid phase over fixed-bed supported palladium catalysts with the addition of carbon monoxide (CO) to the hydrogenation hydrogen.

The hydrogenation of alkynes to alkenes is of major industrial importance and is therefore the subject of extensive prior art.

Thus, GB A 871 804 describes an improved partial hydrogenation of acetylene compounds by the suspension procedure using a palladium catalyst (Pd catalyst) which was doped with salt solutions of the metals Zn, Cd, Hg, Ga, In or Tl.

Furthermore, DE A 24 31 929 describes a process for the preparation of 2-butene-1,4-diol by hydrogenation of butynediol in aqueous solution over a catalyst which contains Pd and one of the elements Zn or Cd and at least one of the elements Bi or Te. The catalyst support used is pumice or alumina.

For the partial hydrogenation of the triple bond in intermediates for vitamins and fragrances, lead-doped Pd catalysts, i.e. Lindlar catalysts, are usually used (cf. for example U.S. Pat. No. 2,681,938).

Frequently, these Lindlar catalysts are also deactivated by means of sulfur compounds in order to increase the selectivity (cf. JP A 120 657/81).

U.S. Pat. No. 2,809,215 describes the batchwise hydrogenation of 3,7,11-trimethyl-6-dodecen-1-yn-3-ol over these Lindlar catalysts.

Finally, DE A 26 19 660 discloses a process for the preparation of butenediol, in which butynediol in an inert solvent is hydrogenated in the presence of a catalyst which contains metallic Pd treated with carbon monoxide. This process can additionally be carried out in the presence of from about 200 to 2000 ppm of CO in the hydrogenation hydrogen.

Furthermore, the use of a $Pd/BaSO_4$ catalyst for the preparation of butenediol is disclosed from DE A 26 05 241.

An overview of the industrially used catalyst systems for the partial hydrogenation of triple bonds to give olefinic double bonds is known from M. Freifelder, "Practical Catalytic Hydrogenation", Wiley Interscience, New York, 1971, pages 84 to 126.

All stated processes have the disadvantage that a suspended catalyst having a high Pd content is used. After the hydrogenation is complete, the catalyst must be separated off from the reaction product by settling and filtration.

It has been found that, on the industrial scale, complete removal of the catalyst powder is possible only at very great expense. However, traces of catalyst residues in the end product give rise to difficulties during the further processing or during the other use of the alkenes. There has therefore been no lack of attempts to develop a fixed-bed catalyst having high abrasion resistance to the partial hydrogenation of the triple bond in alkynes in the liquid phase.

EP 0 841 314 describes a process for the hydrogenation of 3,7,11,15-tetramethyl-1-hexadecyn-3-ol (dehydroisophytol), which is carried out over amorphous metal alloys, such as $Pd_{81}Si_{19}$, in supercritical carbon dioxide, which have been doped with Pb in order to increase the selectivity in the hydrogenation to isophytol. In addition, a sulfur compound, such as 1,2-bis(2-hydroxyethylthio) ethane, had to be added to the hydrogenation mixture in this process, in order to achieve a good yield. The expensive catalyst preparation, the removal and recycling of the carbon dioxide and the additional use of a sulfur-containing compound made the process appear very expensive.

EP 0 412 415 discloses a fixed-bed catalyst for the hydrogenation of 3,7-dimethyloct-1-yn-3-ol (hydrodehydrolinalool) to 3,7-dimethyloct-1-en-3-ol (hydrolinalool), which catalyst contains palladium as an active component and metals such as Sn, Pb, Zn, Cd, Sb or Bi as an inhibitor. The monolithic fixed-bed palladium catalysts described in this patent and doped with inhibitor make it possible to replace the disadvantageous suspension procedure by the technically substantially more advantageous trickle-bed or liquid-phase procedure over the fixed-bed catalyst. The very high abrasion resistance of these catalyst monoliths permits a very high gas and liquid loading.

Unfortunately, it has been found that, when a process described in this patent is carried out continuously over bismuth-doped fixed-bed palladium catalysts over relatively long periods, the selectivity of the hydrogenation of hydrodehydrolinalool to hydrolinalool slowly decreases, i.e. the reaction product contains increasing amounts of the completely hydrogenated 3,7-dimethyloctan-3-ol, which is due to the fact that the bismuth dopant is lost.

EP 754 664 A states that the process according to EP B1 412 415 can be improved by metering small amounts of CO into the hydrogenation gas. The disadvantage of this process is that the space-time yields are still not optimum and that, in the continuous procedure on an industrial scale, the catalysts are not stable and not sufficiently selective over a sufficiently long time.

In the processes according to EP 754 664, EP 0 841 314 and EP 412 415, attention is not paid to the fact that, in the hydrogenation of alkynes, high boilers which adversely affect the overall selectivity always form as a result of oligomerization. However, this formation of high boilers is known from the literature (cf. G. Ertl et al. in "Handbook of Heterogeneous Catalysis", VCH, 1997, page 2172) and is also described in EP 0 827 944.

EP 827 944 describes a process for the hydrogenation of polyunsaturated $C_2$–$C_8$-hydrocarbons over the fixed-bed catalysts disclosed in EP 412 415, the dopants being selected from a relatively large group of metals and the catalyst preparation being extended to include the possibility of impregnating the support materials. However, their use is restricted to $C_2$–$C_8$-hydrocarbons. However, G. Ertl et al. in "Handbook of Heterogeneous Catalysis", VCH, 1997, pages 2202–2204, discloses that the selectivity in the partial hydrogenation of alkynes depends to a great extent on the alkyne to be hydrogenated, since factors such as mass transfer and heat transfer, adsorption and surface reactions on the catalyst greatly affect the selectivity. It is precisely the factors of mass transfer and heat transfer that depend on the viscosity of the reaction medium (cf. for example M. Baerns, H. Hofmann, A. Renken in "Chemische Reaktionstechnik", Georg Thieme Verlag Stuttgart, 2nd edition, 1992, pages 67–97), which is generally high for molecules of relatively high molecular weight.

It is an object of the present invention to provide a process for the preparation of alkenes having relatively high molecular weights, i.e. alkenes of about 10 to 30 carbon atoms, preferably monosubstituted alkenes of 10 to 30 carbon atoms, by partial hydrogenation of the corresponding alkynes, which does not have the disadvantages of the suspension procedure, is technically simple to implement and operates with catalysts which are simple to prepare, have long-term stability, have a high overall selectivity and produces very little overhydrogenated products and high boilers.

We have found, surprisingly, that this object is achieved and that monolithic fixed-bed supported palladium catalysts which were obtained by impregnating the heated support material with a palladium salt solution and have been described in EP 0 827 944 for the partial hydrogenation of low molecular weight alkynes can be used with good selectivities for $C_{10}$- to $C_{30}$-alkynes, too, if amounts of CO which are in the range from 10 to 2000 ppm are added to the hydrogenation hydrogen or the alkyne to be hydrogenated is mixed with the compound which decomposes to a small extent with CO elimination but otherwise does not further intervene in the hydrogenation.

The present invention accordingly relates to a process for the preparation of alkenes by partial hydrogenation of alkynes in the liquid phase at from 20 to 250° C. and hydrogen partial pressures of from 0.3 to 200 bar over fixed-bed supported palladium catalysts which are obtainable by heating the support material in the air, cooling, applying a palladium compound and, if required, additionally other metal ions for doping purposes, molding and processing to give monolithic catalyst elements, wherein A) alkynes of 10 to 30 carbon atoms are used as starting compounds, B) the palladium compound and, if required, the other metal ions are applied to the support material by impregnation of the heated and cooled support material with a solution containing palladium salts and, if required, other metal ions and subsequent drying, and C) from 10 to 2000 ppm of carbon monoxide (CO) are added to the hydrogenation gas or a corresponding amount of CO is allowed to form in the liquid phase by slight decomposition of a compound which is added to the reaction mixture and eliminates CO under the reaction conditions.

The process is particularly suitable for the partial hydrogenation of monosubstituted alkynes, such as 3,7-dimethyloct-6-en-1-yn-3-ol (dehydrolinalool) or 3,7-dimethyloct-1-en-3-ol (hydrodehydrolinalool). The partial hydrogenation of monosubstituted alkynes is known to be substantially more problematic than that of disubstituted alkynes, such as butyne-1,4-diol, since the monosubstituted alkynes can react further during the hydrogenation. Accordingly, the partial hydrogenation of disubstituted alkynes, such as butyne-1,4-diol, is also possible using the novel process.

Examples of suitable starting materials for the novel process are:

Monosubstituted alkynes, such as dehydrolinalool, hydrodehydrolinalool, 1-ethynyl-2, 6, 6-trimethylcyclohexanol and 17-ethynylandrost-5-ene-3β, 17β-diol, 3,7,11,15-tetramethyl-1-hexadecyn-3-ol (dehydroisophytol), 3,7,11-trimethyldodec-1-yn-3-ol, 3,7,11-trimethyl-4-dodecen-1-yn-3-ol and 3,7,11-trimethyl-6-dodecen-1-yn-3-ol (dehydrodihydronerolidol) and disubstituted alkynes, such as 4-methyl-4-hydroxy-2-decyne, 1,1-diethoxy-2-octyne and bis (tetrahydro-2-pyranyloxy)-2-butyne.

The starting compounds can also be used in the form of a mixture of two or more different alkynes. The individual alkenes can then be separated in a manner known per se, for example by distillation, from the resulting mixture of various alkenes.

If the starting alkynes were prepared by reacting acetylene with a ketone, the unreacted ketone may be present as a mixture with the alkynes in the novel process. This even has the advantage that the ketone is capable of eliminating small amounts of CO, which can make the metering in of CO superfluous.

Woven fabrics of inorganic materials, such as $Al_2O_3$ and/or $SiO_2$, or woven fabrics of wires comprising plastics, such as polyamides, polyesters, polypropylene, polytetrafluoroethylene, etc., may be used as catalyst support material. However, foil-like or fabric-like metal supports, i.e. foils or woven wire fabrics comprising metals, such as iron, spring steel, copper, brass, aluminum, nickel silver, nickel, chromium steel or chromium nickel steels, are particularly suitable. Foils or woven fabrics of materials having material numbers 1.4767, 1.4401 and 1.4301 have proven particularly useful. The designation of these materials with the stated material numbers is in line with the material numbers stated in the Stahleisenliste, published by the Verein Deutscher Eisenhuttenleute; $8^{th}$ edition, pages 87, 89 and 106, Verlag Stahleisen mbH, Dusseldorf 1990. The material having material number 1.4767 is also known under the name Kanthal. These metallic supports are pretreated by oxidative heating, preferably in the air, at from 600 to 1100° C., preferably from 700 to 1000° C.

The application of the palladium is carried out by simple impregnation of the support material with Pd-containing solutions which are prepared by dissolving salts of palladium with inorganic or organic acids, preferably nitrates, in a solvent, preferably water. The metal salt solution may furthermore contain one or more promoter elements, which may originate from groups II to V and IB to VIIIB of the Periodic Table of the Elements. Particularly preferably used dopant metals are Cu, Ag and Au. The impregnation is followed by a drying step in which the woven fabric is preferably moved. This is followed by a calcination step.

The amounts of applied Pd may be from 5 to 1000, preferably from 30 to 500, mg/m$^2$ of fabric area. The amounts of the additional promoters are in general from about 0.5 to 800, preferably from 1 to 500, mg/m$^2$ of fabric area.

The support material coated in this manner with palladium can then be formed by heating at from 200 to 800° C., preferably from 300 to 700° C., for from 0.5 to 2 hours. Depending on the type of palladium coating, this heating step after the coating can however also be omitted. The catalyst foils, catalyst nets or woven fabric coated in this manner with Pd and, if required, subsequently heated are then expediently molded in a manner known per se to give monoliths or moldings, e.g. Sulzer packings, for installation in the hydrogenation reactor. This makes it possible to establish the desired good flow conditions in the reactor.

After the reduction of the catalyst with hydrogen at from 20 to 250° C., preferably from 70 to 200° C., which is advantageously carried out in the reactor, the catalyst is ready for use for the novel partial hydrogenation.

The novel process is advantageous if the partial hydrogenation is carried out continuously in a tube reactor by the trickle-bed or liquid phase procedure with product recycling with cross-sectional loading of from 20 to 500, preferably from 100 to 300, m$^3$/m$^2$*h.

It is also very advantageous if, like the liquid product, the hydrogenation gas mixture comprising hydrogen and CO is also circulated with similar cross-sectional loadings.

The rate of hydrogen absorption is a measure of selectivity. If too much hydrogen is reacted per unit time, a high proportion of overhydrogenated byproduct is obtained; if too little hydrogen is reacted per unit time, a high proportion of oligomeric, high-boiling byproducts is obtained. Since the rate of hydrogen absorption is dependent on the CO concentration in the hydrogenation mixture, the novel process opens up the very advantageous possibility of establishing the selectivity by means of the CO metering.

The partial hydrogenation is particularly advantageous on an industrial scale if it is carried out by the liquid phase procedure and the cycle gas is sprayed in very fine distribution into the reactor by means of the liquid stream and a suitable apparatus, such as a liquid-gas compressor. In conjunction with the shaping of the catalyst monoliths and the described gassing of the reactor, high space-time yields are achieved by optimum cross-mixing and good hydrodynamics of the catalyst interface. The partial hydrogenations are carried out at from 20 to 250° C., preferably from 60 to 200° C., depending on the substance.

The partial hydrogenation is advantageously carried out continuously in one or more reactors connected in series. The hydrogen partial pressure is in general from 0.3 to 200, preferably from 0.5 to 20, bar. The hydrogenations can be carried out with or without exit gas.

With the aid of the novel process, it is possible to prepare many alkenes required as fragrances or intermediates for active ingredients, such as vitamins, in particular monosubstituted alkenes, such as linalool, hydrolinalool, 3,7,11,15-tetramethyl-1-hexadecen-3-ol (isophytol), 3,7,11-trimethyl-1-dodecen-3-ol (tetrahydronerolidol), 3,7,11-trimethyl-1,4-dodecadien-3-ol or 3,7,11-trimethyl-1,6-dodecadien-3-ol (dihydronerolidol), from the corresponding alkynes in good yields and good space-time yields and with constantly good selectivities, also on an industrial scale, in a continuous process over catalysts which can be relatively easily prepared, contain only a small amount of Pd, are abrasion-resistant and are stable over long periods.

The procedure for the catalyst preparation and that for the novel partial hydrogenation are illustrated in comparison with those according to the most closely related prior art, by means of the following examples.

EXAMPLE 1

(Comparative Example)

A. Catalyst preparation by vapor deposition on woven metal fabric

A smooth woven Kanthal fabric (material number 1.4767) having a mesh size of 180 μm and a wire diameter of 112 μm was heated in the air for 5 hours (h) at 950° C. A 20 cm wide fabric strip was clamped on the winding apparatus installed in an ultra high vacuum vapor deposition unit and then coated continuously with 2 nm of Pd at $10^{-6}$ mbar by vapor deposition. By rewinding the fabric, the latter was coated with 0.7 nm of Bi in a second vapor deposition step. After the vapor deposition, the catalyst intermediate was formed for 30 minutes (min) at 600° C. in an electric muffle furnace. For this purpose, the heating furnace was heated to 600° C. in the course of 40 minutes, kept at this temperature for 30 minutes and then switched off. After cooling, the catalyst was removed from the muffle furnace and shaped into a monolith.

B. Batchwise selective hydrogenation of 3,7,11,15-tetramethyl-1-hexadecyn-3-ol (dehydroisophytol) to 3,7,11,15-tetramethyl-1-hexadecen-3-ol (isophytol) without the supply of CO.

The supported Pd/Bi catalyst prepared according to Example 1A, in the form of a metal monolith having a diameter of 13.2 mm and a height of 200 mm, was introduced into a tube reactor. 300 g of a mixture of dehydroisophytol containing about 18% by weight of 6,10,14-trimethylpentadecan-2-one (hexahydrofarnesylacetone) were passed over the catalyst by the liquid phase procedure with recycling with a cross-sectional loading of 200 $m^3/m^2$*h. Hydrogen was circulated at a partial pressure of 2 bar, simultaneously with the liquid stream. In the exit gas, whose composition corresponded to that of the cycle gas, a CO concentration of 20 ppm was measured after 60 minutes, which CO had formed from a ketone since no CO was fed in. At 110° C., complete conversion was achieved after 170 min. The overall selectivity was 93.2%, the byproducts being distributed over overhydrogenated product and residue in the ratio of 1:2.8.

EXAMPLE 2

A. Catalyst preparation

The same smooth Kanthal fabric as in Example 1A was heated for 5 h at 900° C. in the presence of air. A 20 cm wide fabric strip was clamped on a winding apparatus and then transported continuously through an impregnation bath which contained an aqueous metal salt solution comprising palladium nitrate and silver nitrate. The subsequently dried fabric strip had a coating of 73 mg of $Pd/m^2$ and 18 mg of $Ag/m^2$. The catalyst intermediate was formed for 3 h at 300° C. in an electric muffle furnace. The catalyst was then shaped into a monolith as described in Example 1A.

B. Batchwise selective hydrogenation of dehydroisophytol to isophytol without the supply of CO.

Supported Pd/Ag catalyst prepared according to Example 2A, in the form of a metal monolith having a diameter of 13.2 mm and a height of 200 mm, was introduced into a tube reactor. 300 g of a mixture of dehydroisophytol containing about 18% by weight of hexahydrofarnesylacetone were passed over the catalyst by the liquid phase procedure with recycling with a cross-sectional loading of 200 $m^3/m^2$ *h. Hydrogen was circulated at a partial pressure of 2 bar, simultaneously with the liquid stream. In the exit gas, whose composition corresponded to that of the cycle gas, a CO concentration of 20 ppm was measured after 60 min, which CO must have been formed from the ketone since no CO was fed in. At 110° C., complete conversion was achieved after 125 min. The overall selectivity was 95.0% of theory, byproducts being distributed over overhydrogenated product and residue in the ratio 1:0.54.

EXAMPLE 3

A. Catalyst preparation

The same smooth Kanthal fabric as in Example 1A was heated for 5 h at 900° C. in the presence of air. A 20 cm wide fabric strip was clamped on a winding apparatus and then transported continuously through an impregnation bath which contained an aqueous metal salt solution comprising palladium nitrate and silver nitrate. The subsequently dried fabric strip had a coating of 146 mg of $Pd/m^2$ and 73 mg of $Ag/m^2$. The catalyst intermediate was then formed and shaped into a monolith, these steps being carried out as described in Example 2A.

B. Batchwise selective hydrogenation of 3,7,11-trimethyl-6-dodecen-1-yn-3-ol (dehydrodihydronerolidol) to 3,7,11-trimethyl-1,6-dodecadien-3-ol (dihydronerolidol) without the supply of CO.

The Pd/Ag catalyst prepared according to Example 3A, in the form of a metal monolith having a diameter of 13.2 mm and a height of 200 mm, was introduced into a tube reactor. 300 g of a mixture comprising dehydrodihydronerolidol and containing about 36% by weight of 6,10-dimethyl-5-undecan-2-one (H-geranylacetone) were passed over the catalyst by the liquid phase procedure with recycling with a cross-sectional loading of 200 $m^3/m^2*h$. Hydrogen was circulated at a partial pressure of 2 bar, simultaneously with the liquid stream. In the exit gas, whose composition corresponded to the cycle gas, a CO concentration of 20 ppm was measured after 60 min, which CO must have been formed from the ketone since no CO was fed in. At 110° C., complete conversion was achieved after 180 min. The overall selectivity was 93.6%, the byproducts being distributed over overhydrogenated product and residue in the ratio 1:1.1.

EXAMPLE 4

A. Catalyst preparation

The catalyst preparation was carried out as in Example 2A, except that the monoliths prepared from the fabric had different dimensions.

B. Batchwise selective hydrogenation of dehydroisophytol to isophytol without the supply of CO.

20 monoliths of the Pd/Ag catalyst prepared according to Example 4A and having a diameter of 35 mm and a height of 50 mm were introduced into a tube reactor. 2200 g of a mixture comprising dehydroisophytol and containing about 18% by weight of hexahydrofarnesylacetone were passed over the catalyst by the liquid phase procedure with recycling with cross-sectional loading of 200 $m^3/m^2*h$. Hydrogen was circulated at a partial pressure of 2 bar, simultaneously with the liquid stream. In the exit gas, whose composition corresponded to that of the cycle gas, a CO concentration of 96 ppm was measured after 45 min, which CO must have been formed from the ketone as no CO was fed in. At 98° C., complete conversion was achieved after 60 min. The overall selectivity was 94% of theory, the byproducts being distributed over overhydrogenated product and residue in the ratio 1:0.24.

EXAMPLE 5

A. Catalyst preparation

The catalyst preparation was carried out as described in Example 2A, except that the monoliths prepared from the fabric had different dimensions.

B. Continuous selective hydrogenation of dehydrodihydronerolidol to dihydronerolidol.

Four monoliths of the Pd/Ag catalyst prepared according to Example 4A and having a diameter of 35 mm and a height of 200 mm and one monolith having a diameter of 35 mm and a height of 100 mm were introduced into a tube reactor. A second tube reactor was filled with 5 monoliths having a diameter of 27 mm and a height of 50 mm. The first reactor was operated by the liquid phase procedure with recycling with a liquid cross-sectional loading of 200 $m^3/m^2*h$ and a hydrogen cross-sectional loading of 200 $m^3/m^2*h$ at a total pressure of 7 bar. CO was metered into the hydrogen in an amount such that the exit gas, whose composition corresponded to that of the cycle gas, had a CO concentration of from 1200 to 1500 ppm. The temperature in the first reactor was 110° C. The feed rate of a mixture comprising dehydrodihydronerolidol and containing about 18% by weight of 6,10-dimethylundecan-2-one (H-geranylacetone) corresponded to the removal rate from the circulation of the first reactor, which was fed continuously to the second reactor. The second reactor was operated by the liquid phase procedure in a straight pass at from 4 to 5 bar, from 70 to 95° C. and a CO concentration in the hydrogen of from 1000 to 1500 ppm. After a run-time of 318 h, an overall selectivity of 95.4% was achieved in the first reactor at a conversion of 95.4%. The remaining conversion was realized in the second reactor (downstream reactor). The overall reactivity was then 96.2%, the byproducts being distributed over overhydrogenated product and residue in the ratio 1:1.0. The space-time yield was 0.62 1 per 1 of catalyst per h.

After a run-time of 732 h an overall selectivity of 97.0% was achieved in the first reactor at a conversion of 92.8%. The remaining conversion was realized in the downstream reactor. The overall selectivity was then 97.4%, the byproducts being distributed over overhydrogenated product and residue in the ratio 1:1.1. The space-time yield was 0.76 1 per 1 of catalyst per h. This shows that the catalyst used is subject to neither deactivation nor deterioration in the selectivity over a long period.

EXAMPLE 6

A. Catalyst preparation

The catalyst preparation was carried out as described in Example 2A, except that the monoliths prepared from the fabric had different dimensions.

B. Continuous selective hydrogenation of 3,7-dimethyloct-1-en-3-ol.(hydrodehydrolinalool) to 3,7-dimethyloct-1-en-3-ol (linalool).

20 monoliths of the Pd/Ag catalyst prepared according to Example 4A and having a diameter of 35 mm and a height of 50 mm were introduced into a tube reactor. The second tube reactor was filled with 10 monoliths having a diameter of 27 mm and a height of 50 mm. The first reactor was operated by the liquid phase procedure with recycling with a liquid cross-sectional loading of 200 $m^3/m^2*h$ and a hydrogen cross-sectional loading of 200 $m^3/m^2*h$ at a total pressure of 7 bar. CO was metered into the hydrogen in an amount such that the exit gas, whose composition corresponded to that of the cycle gas, had a CO concentration of from 1200 to 1500 ppm. The temperature in the first reactor was 104° C. The amount of hydrogenation mixture fed to the second reactor was taken from the circulation of the first reactor. The second reactor was operated by the liquid phase procedure in a straight pass at from 4 to 5 bar, 70° C. and a CO concentration in the hydrogen of from 200 to 500 ppm. After a run-time of 22 hours, an overall selectivity of 95.3% was achieved in the first reactor at a conversion of 95.4%. The remaining conversion was realized in the downstream reactor. The overall selectivity was then 94.8%, the byproducts being distributed over overhydrogenated product and residue in the ratio 1:0.93. The space-time yield was 1.01 1 per 1 of catalyst per h.

EXAMPLE 7

Comparative Example for Example 6

A. Catalyst preparation

The catalyst preparation took place analogously to Example 1A, except that the monoliths prepared from the fabric had different dimensions.

B. Continuous selective hydrogenation of hydrodehydrolinalool to linalool.

20 monoliths of the Pd/Bi catalyst prepared according to Example 1A and having a diameter of 35 mm and a height of 50 mm were introduced into a tube reactor. A second tube reactor was filled with 20 monoliths having a diameter of 27 mm and a height of 50 mm. The first reactor was operated by the liquid phase procedure with recycling with a liquid cross-sectional loading of 200 $m^3/m^2*h$ and a hydrogen cross-sectional loading of 200 $m^3/m^2*h$ at a total pressure of 6 bar. CO was metered into the hydrogen in an amount such that the exit gas, whose composition corresponded to that of the cycle gas, had a CO concentration of from 100 to 300 ppm. The temperature in the first reactor was 90° C. The amount of hydrogenation mixture fed to the second reactor was taken from the circulation of the first reactor. The second reactor was operated by the liquid phase procedure in a straight pass at from 4 to 5 bar, 70° C. and a CO concentration in the hydrogen of from 50 to 150 ppm. After a run-time of 100 hours, an overall selectivity of 90.6% was achieved in the first reactor at a conversion of 87.9%. The remaining conversion was realized in the downstream reactor. The overall selectivity was then 90.4%, the byproducts being distributed over overhydrogenated product and residue in the ratio 1:1.6. The space-time yield was 0.36 1 per 1 of catalyst per h.

EXAMPLE 8

A. Catalyst preparation

The catalyst preparation took place analogously to Example 2A, except that the monoliths prepared from the fabric had different dimensions.

B. Continuous selective hydrogenation of dehydroisophytol to isophytol.

Four monoliths of the Pd/Ag catalyst prepared according to Example 8A and having a diameter of 35 mm and a height of 200 mm and one monolith having a diameter of 35 mm and a height of 100 mm were introduced into a tube reactor. A second tube reactor was filled with 5 monoliths having a diameter of 27 mm and a height of 50 mm. The first reactor was operated by the liquid phase procedure with recycling with a liquid cross-sectional loading of 200 $m^3/m^2$*h and a hydrogen cross-sectional loading of 200 $m^3/m^2$*h at a total pressure of 7 bar. CO was metered into the hydrogen in an amount such that the exit gas, whose composition corresponded to that of the cycle gas, had a CO concentration of from 800–900 ppm. The temperature in the first reactor was 103° C. The amount of a mixture of dehydroisophytol comprising approximately 12% by weight of 6,10,14-trimethylpentadecan-2-one (hexahydrofarnesylacetone) fed continuously to the second reactor corresponded to the amount withdrawn from the circulation of the first reactor. The second reactor was operated by the liquid phase procedure in a straight pass at from 4 to 5 bar, 110° C. and a CO concentration in the hydrogen of from in the region of 100 ppm. After a run-time of 754 hours, an overall selectivity of 96.1% was achieved in the first reactor at a conversion of 97.4%. The remaining conversion was realized in the second reactor (downstream reactor). The overall selectivity was then 96.7%, the byproducts being distributed over overhydrogenated product and residue in the ratio 1:0.38. The space-time yield was 0.67 1 per 1 of catalyst per h.

EXAMPLE 9

A. catalyst preparation

The same smooth Kanthal fabric as in Example 1A was heated in the presence of air for 5 hours at 900° C. A 20 cm wide fabric strip was clamped on a winding apparatus and then transported continuously through an impregnation bath containing an aqueous metal salt solution of palladium nitrate and silver nitrate. The subsequently dried fabric strip had a coating of 278 mg of $Pd/m^2$ and 70 mg of $Ag/m^2$. The catalyst precursor was subsequently formed as described in Example 2A and shaped into a monolith.

B. Batchwise selective hydrogenation of 3,7,11-trimethyldodec-1-yn-3-ol to 3,7,11-trimethyl-1-dodecen-3-ol (tetrahydronerolidol) without the supply of CO.

The Pd/Ag catalyst prepared according to Example 9A, in the form of a metal monolith having a diameter of 13.2 mm and a height of 200 mm, was introduced into a tube reactor. 300 g of a mixture of 3,7,11-trimethyldodec-1-yn-3-ol containing about 2% by weight of 6,10-dimethylundecan-2-one (TH-geranylacetone) was passed over the catalyst by the liquid phase procedure with recycling with a cross-sectional loading of 200 $m^3/m^2$*h. Hydrogen was circulated at a partial pressure of 2 bar, simultaneously with the liquid stream. In the exit gas, whose composition corresponded to that of the cycle gas, a CO concentration of 20 ppm was measured after 60 minutes, which CO had formed from the ketone since no CO was fed in. At 110° C., complete conversion was achieved after 165 min. The overall selectivity was 94.5%, the byproducts being distributed over overhydrogenated product and residue in the ratio of 1:0.47.

We claim:

1. A process for the preparation of alkenes by partial hydrogenation of alkynes in the liquid phase at from 20 to 250° C. and hydrogen partial pressures of from 0.3 to 200 bar over fixed-bed supported palladium catalysts which are obtainable by heating the support material in the air, cooling, applying a palladium compound and, optionally, other metal ions for doping purposes, molding and processing to give monolithic catalyst elements, wherein A) alkynes of 10 to 30 carbon atoms are used as starting compounds, B) the palladium compound and, optionally, the other metal ions are applied to the support material by impregnation of the heated and cooled support material with a solution containing palladium salts and, if required, other metal ions and subsequent drying, and C) from 10 to 2000 ppm of carbon monoxide (CO) are added to the hydrogenation gas or a corresponding amount of CO is allowed to form in the liquid phase by slight decomposition of a compound which is added to the reaction mixture and eliminates CO under the reaction conditions.

2. A process as claimed in claim 1, wherein the fixed-bed supported palladium catalyst used is a supported catalyst which has been prepared from metallic support material in the form of a metal woven fabric or a metal foil.

3. A process as claimed in claim 1, wherein the compound which eliminates CO under the reaction conditions is contained in the alkyne in amounts of from 0 to 80% by weight.

4. A process as claimed in claim 1, wherein mixtures of two or more different alkynes are used as the starting compound and the individual alkenes are separated from the resulting mixture of different alkenes by distillation in a manner known per se.

5. A process as claimed in claim 1, which is used for the preparation of 3,7,11,15-tetramethyl-1-hexadecen-3-ol (isophytol), 3,7,11-trimethyl-1-dodecen-3-ol (tetrahydronerolidol), 3,7,11-trimethyl-1,4-dodecadien-3-ol or 3,7,11-trimethyl-1,6-dodecadien-3-ol (dihydronerolidol) from the corresponding alkynes.

6. A process as claimed in claim 3, which is used for the preparation of 3,7-dimethyloct-1,6-dien-3-ol or 3,7-dimethyloct-1-en-3-ol from the corresponding alkynes.

7. A process as claimed in claim 1, wherein the partial hydrogenation is carried out in a tube reactor by the trickle-bed or liquid phase procedure with product recycling at cross-sectional loadings of from 20 to 500 $m^3/m^2$.h.

8. A process as claimed in claim 7, wherein the hydrogenation gas mixture comprising hydrogen and CO is circulated and the hydrogen absorption, and hence the selectivity, are controlled by means of the CO metering.

9. A process as claimed in claim 7, wherein the partial hydrogenation is carried out by the liquid phase procedure and the cycle gas is injected into the reactor by means of a suitable apparatus in very fine distribution.

10. A process as claimed in claim 1, wherein the partial hydrogenation is carried out at a hydrogen partial pressure of from 0.5 to 20 bar.

11. A process as claimed in claim 1, wherein the partial hydrogenation is carried out continuously in one or more reactors connected in series.

12. A process as claimed in claim 1 wherein a fixed-bed supported catalyst is used which is obtainable by subsequently heating it for forming after coating of the support material with palladium.

* * * * *